(12) United States Patent
Sasaki et al.

(10) Patent No.: US 8,016,805 B2
(45) Date of Patent: Sep. 13, 2011

(54) PULL-ON DISPOSABLE DIAPER

(75) Inventors: Jun Sasaki, Tochigi (JP); Taeko Kanai, Tochigi (JP); Michiko Otsuka, Tokyo (JP)

(73) Assignee: KAO Corporation, Tokyo (JP)

( * ) Notice: Subject to any disclaimer, the term of this patent is extended or adjusted under 35 U.S.C. 154(b) by 514 days.

(21) Appl. No.: 11/192,182

(22) Filed: Jul. 29, 2005

(65) Prior Publication Data

US 2006/0025746 A1 Feb. 2, 2006

(30) Foreign Application Priority Data

Jul. 30, 2004 (JP) .................................. 2004-224838
Jul. 30, 2004 (JP) .................................. 2004-224894

(51) Int. Cl.
*A61F 13/15* (2006.01)

(52) U.S. Cl. ......... 604/385.29; 604/385.24; 604/285.25; 604/385.26; 604/385.3; 604/393; 604/396

(58) Field of Classification Search .. 604/385.24–385.3, 604/393–396
See application file for complete search history.

(56) References Cited

U.S. PATENT DOCUMENTS

| | | | | |
|---|---|---|---|---|
| 3,860,003 A | * | 1/1975 | Buell | 604/385.25 |
| 4,578,072 A | * | 3/1986 | Lancaster | 604/385.24 |
| 5,221,274 A | | 6/1993 | Buell et al. | |
| 5,368,584 A | | 11/1994 | Clear et al. | |
| RE34,920 E | * | 4/1995 | Aziz et al. | 604/385.25 |
| 5,817,087 A | | 10/1998 | Takabayashi et al. | |
| 2002/0049421 A1 | | 4/2002 | Hayase et al. | |
| 2002/0095132 A1 | | 7/2002 | Ashton et al. | |
| 2002/0151863 A1 | | 10/2002 | Toyoshima | |

FOREIGN PATENT DOCUMENTS

| | | |
|---|---|---|
| CN | 1341408 A | 3/2002 |
| EP | 0 323 634 A2 | 7/1989 |
| EP | 547497 A2 * | 6/1993 |
| EP | 0753292 A2 | 1/1997 |
| EP | 0806196 B1 | 11/1997 |
| EP | 0901782 A2 | 3/1999 |
| EP | 1184012 B1 | 3/2002 |
| EP | 1384459 A2 | 1/2004 |

(Continued)

OTHER PUBLICATIONS

Japanese Office Action issued in JP2005-204971 on Nov. 24, 2009.

(Continued)

*Primary Examiner* — Jacqueline F. Stephens
(74) *Attorney, Agent, or Firm* — Birch, Stewart, Kolasch & Birch, LLP

(57) ABSTRACT

A pull-on disposable diaper 1 has, between a waist opening 5 and leg openings 6, a region 71 having a width of 15 to 35 mm in each of a front section A and a rear section B. The region 71, while worn by a wearer, applies a pressure of 1.1 to 2.5 kPa to the wearer's body. With the diaper 1 opened and stretched out, the distance from the longitudinal centerline of the diaper to the widthwise middle of the region 71 in the front section A is 180 to 220 mm, and the distance from the longitudinal centerline of the diaper to the widthwise middle of the region 71 in the rear section B is 180 to 220 mm. A waist portion around the waist opening 5, while worn by a wearer, applies a pressure of 0.3 to 1.5 kPa to the wearer's body.

10 Claims, 6 Drawing Sheets

FOREIGN PATENT DOCUMENTS

| | | |
|---|---|---|
| EP | 1452157 A1 | 9/2004 |
| JP | 6-421 U | 1/1994 |
| JP | 9-84826 A | 3/1997 |
| JP | 9-511425 | 11/1997 |
| JP | 11-155901 A | 6/1999 |
| JP | 11-253489 | 9/1999 |
| JP | 2001-87311 A | 4/2001 |
| JP | 2001-258931 A | 9/2001 |
| JP | 2002-11039 A | 1/2002 |
| JP | 2002-336302 | 11/2002 |
| JP | 2005-168833 A | 6/2005 |
| TW | 00342326 | 10/1998 |
| WO | WO-95/29657 A1 | 11/1995 |
| WO | WO-99/60968 A1 | 12/1999 |
| WO | WO-99/65442 A1 | 12/1999 |
| WO | WO-01/74280 A1 | 10/2001 |
| WO | WO-2004/066897 A1 | 8/2004 |

OTHER PUBLICATIONS

Japanese Office Action issued in JP2005-204974 on Dec. 1, 2009.

* cited by examiner

PULL-ON DISPOSABLE DIAPER

TECHNICAL FIELD

The present invention relates to pull-on disposable diapers, particularly those for older babies and toddlers.

BACKGROUND ART

Pull-on (also called pants type) disposable diapers having elastic members disposed between the waist opening and the leg openings to develop extensibility in the diaper width direction are known. For example, JP-A-9-84826 proposes a pull-on type disposable diaper, at least the front section of which has a first portion within an area 20 mm above the front end of the absorbent core and 20 mm below the front end of the absorbent core and a second portion defined between the first portion and the leg openings, wherein elastic members are spacedly disposed at a smaller interval in the first portion than in the second portion. The proposal aims at leak prevention without impairing the wearing comfort by making the contact with the wearer's body closer in the first portion than in the second one while substantially equalizing the planar pressure per given area between the first and the second portions.

A pull-on disposable diaper having elastic members disposed at an interval gradually decreasing toward the waist opening is also known from JP-A-U-6-421. This configuration allows for a strong contracting force being applied on the upper part of the wearer's hipbone.

However, the above-described configurations tend to make the diapers difficult to put on because of a strong constrictive force exerted in the waist portion. Moreover, the diapers tend to droop while worn, resulting in a sloppy appearance, hindrance to the wearer's movement, and fear of urine and fecal leakage.

DISCLOSURE OF THE INVENTION

The present invention provides a pull-on disposable diaper having a waist opening and a pair of leg openings. The diaper has a front section and a rear section. The diaper further has regions which are located between the waist opening and the leg openings at the front section and the rear section, respectively. The regions, while worn by a wearer, apply a pressure of 1.1 to 2.5 kPa to the wearer's body. The regions have a width of 15 to 35 mm. The distance from the longitudinal centerline of the diaper in its opened and stretched out state to the widthwise middle of the region in the front section is 180 to 220 mm. The distance from the longitudinal centerline of the diaper in its opened and stretched out state to the widthwise middle of the region in the rear section is 180 to 220 mm. A waist portion around the waist opening, while worn by a wearer, exerts a pressure of 0.3 to 1.5 kPa. The term "longitudinal centerline" refers to a hypothetical line which equally divides the diaper along the longitudinal (length) direction of the diaper into two sections in its opened and stretched out state. The pull-on disposable diaper having the above-described characteristics will hereinafter be sometimes referred to as a diaper according to the first aspect of the invention.

The diaper described above may also include an absorbent core, and the regions are located substantially between the lateral side edges of the diaper and the lateral side edges of the absorbent core. The diaper described above may also have the regions located in a region adapted to be applied to the part of a wearer from the iliac crest to the anterior superior iliac spine. The diaper described above may also have a waist portion, while worn by a wearer, that applies a pressure lower than the pressure applied by the regions on the wearer's body.

The present invention also provides a pull-on disposable diaper having a waist opening, a pair of leg openings, and a pair of side seals. The diaper has a total length of 440 to 530 mm and a side seal length of 90 to 140 mm in its opened and stretched out state. The diaper has hypothetically quartered first to fourth subsections having equal widths in the diaper length direction from the waist opening to the leg openings. The second subsection exerts, while worn by a wearer, an average pressure of 0.9 to 1.8 kPa and a maximum pressure of 2.5 kPa or lower to the wearer's body. The first and the third subsections exerts, while worn by a wearer, a lower pressure to the wearer's body than the second subsection. The pull-on disposable diaper having the above-described characteristics will hereinafter be sometimes referred to as a diaper according to the second aspect of the invention.

The present invention also provides a pull-on disposable diaper having a waist opening and a pair of leg openings. The diaper has a front section and a rear section. The diaper further has a first region and a second region at each of the front section and the rear section. The first and second regions are located between the waist opening and the leg openings. The first regions are closer to the waist opening, and the second regions are closer to the leg openings. The regions, while worn by a wearer, apply a pressure to the wearer's body. A waist portion around the waist opening, while worn by a wearer, applies a pressure to the wearer's body that is less than the pressure to the wearer's body applied by the first region but more than the pressure to the wearer's body applied by the second region.

In this embodiment, the first regions of the pull-on disposable diaper may apply a pressure of 1.1 to 2.5 kPa to the wearer's body. The first regions may also have a width of 15 to 35 mm. The distance from a longitudinal centerline of the diaper in the opened and stretched out state to a widthwise middle of the first region in the front section may be 180 to 220 mm. The distance from a longitudinal centerline of the diaper in the opened and stretched out state to a widthwise middle of the first region in the rear section may be 180 to 220 mm. The waist portion of the pull-on disposable diaper may apply a pressure of 0.3 to 1.5 kPa to the wearer's body. The second region of the pull-on disposable diaper may apply a pressure of 0.2 to 0.8 kPa to the wearer's body. The second region may have a width of 40 to 70 mm. The pull-on disposable diaper may also have a crotch section and at least two sets of leg elastic members that overlap in the crotch section.

The present invention also provides a pull-on disposable diaper having a waist opening and a pair of leg openings. The diaper has a front section and a rear section. The diaper further has a first region and a second region at each of the front section and the rear section. The first and second regions are located between the waist opening and the leg openings. The first regions are closer to the waist opening, and the second regions are closer to the leg openings. The regions, while worn by a wearer, apply a pressure to the wearer's body. The diaper also has a waist portion around the waist opening. A pressure applied by the first region is higher than a pressure applied by the waist portion, and a pressure applied by the first region is higher than a pressure applied by the second region.

DETAILED DESCRIPTION OF THE INVENTION

Figure 1:
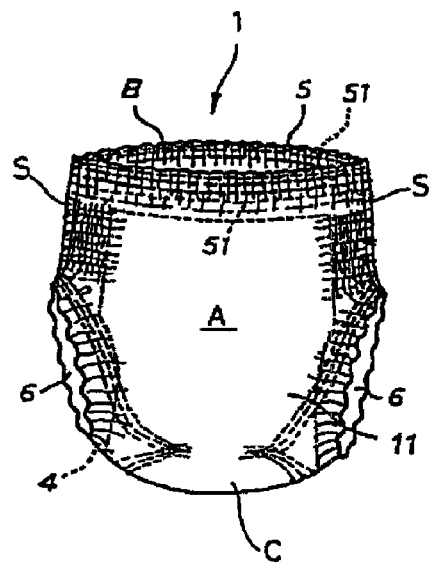
FIG. 1 is a perspective illustrating an embodiment of the pull-on disposable diaper according to the first aspect of the invention.
Figure 2:
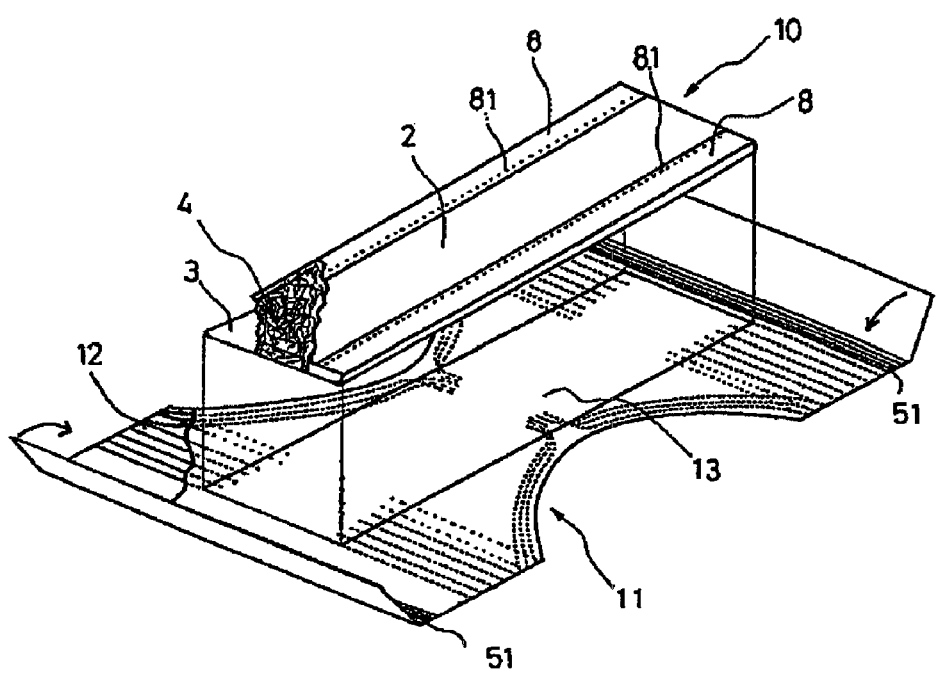
FIG. 2 is a cutaway view illustrating the diaper of FIG. 1 before assembly.
Figure 3:
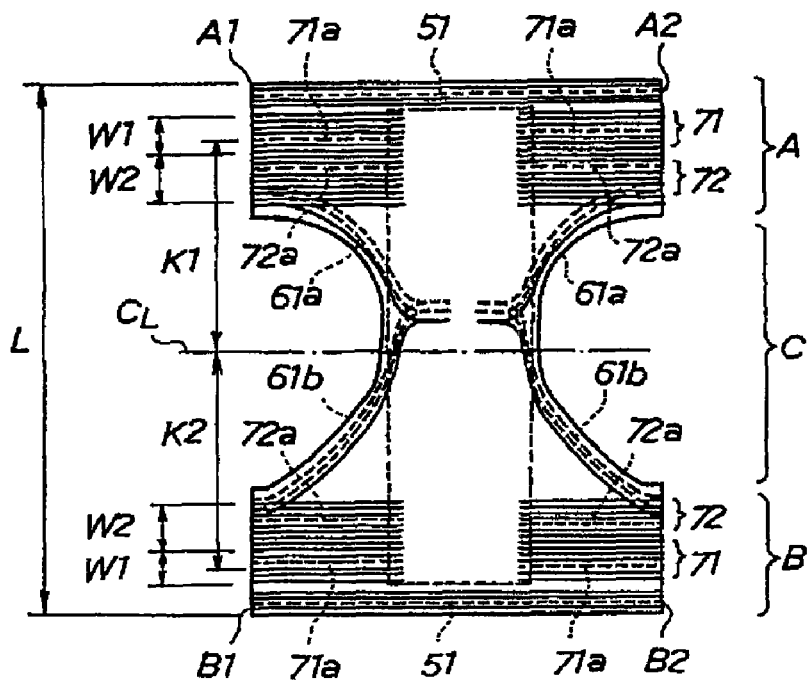
FIG. 3 is a plan of the exterior laminate of FIG. 2 in its opened and stretched out state.

The present invention will be described based on its preferred embodiments with reference to the accompanying drawings. In what follows, the term "present invention" indicates either one or both of the first and the second aspects as referred to above, which depends on the context. FIG. 1 is a perspective view of an embodiment of the pull-on disposable diaper according to the first aspect of the invention. FIG. 2 is a cutaway view illustrating the diaper of FIG. 1 before assembly. FIG. 3 is a plan of the exterior laminate shown in FIG. 2 in its opened and stretched out state. The term "opened state" indicates the state before the lateral side edges of a diaper are connected together to make an underpants shape. The term "sealed state" used infra means the state after the lateral side edges are sealed to make side seals.

The diaper 1 of the embodiment shown in FIGS. 1 through 3 is composed of an absorbent body 10 having a liquid permeable topsheet 2, a water repellant backsheet 3, and a liquid retentive absorbent core 4 interposed between the sheets 2 and 3 and an exterior laminate 11 which is disposed on the backsheet side of the absorbent body 10. The absorbent body 10 has a substantially oblong rectangular shape.

The exterior laminate 11 has its longitudinal middle portion narrowed in a sandglass shape to define the outline of the diaper. The exterior laminate 11 is sectioned into a front section A that is to be located on the wearer's stomach side, a rear section B that is to be located on the wearer's back side, and a crotch section C between the sections A and B. The front section A and the rear section B contain the longitudinal front and rear ends, respectively, and the crotch section C corresponds to the lengthwise middle portion of the exterior laminate 11. The lateral side edges of the front section A and those of the rear section B are joined together by any known means, such as heat sealing, high frequency sealing or ultrasonic sealing, to form a pull-on type diaper having a waist opening and a pair of leg openings. Symbol S in FIG. 1 indicates side seals.

The topsheet 2, the backsheet 3, and the absorbent core 4 are each rectangular and united together to form an oblong rectangular absorbent body 10. The topsheet 2 and the backsheet 3 can be of materials commonly used in this type of diapers. The absorbent core 4 is made of superabsorbent polymer particles and fibrous materials and is enclosed in tissue paper (not shown).

As shown in FIG. 2, a side cuff 8 made of a liquid impermeable or water repellent, breathable material is provided on each long side of the absorbent body 10. The side cuff 8 has its outside edge fixed to the topsheet 2 along the length of the absorbent body 10, with the inside edge free. The fixed edge and the free edge are fixed to the topsheet 2 at both longitudinal ends of the absorbent body 10 (the upper and the lower ends of the absorbent body in FIG. 3). A side cuff elastic member 81 is disposed in its stretched out state in each side cuff 8 along the free edge. After assembly into the diaper 1 shown in FIG. 1, the elastic members 81 contract to cause the pair of the side cuffs 8 to stand thereby to block the flow of liquid in the width direction of the absorbent body 10.

The exterior laminate 11 has at least two sheets of nonwoven fabric, i.e., an outer sheet 12 serving as the outer surface of the diaper 1 (the side opposite to a wearer's side) and an inner sheet 13 on the inner side of the inner sheet 12. The inner sheet 13 is joined to the inner side of the outer sheet 12 with an adhesive, such as a hot-melt adhesive. It is preferred for both the outer sheet 12 and the inner sheet 13 to be of water repellent nonwoven fabric so as to prevent liquid oozing from the outside and the inside of the diaper.

A plurality of waist elastic members 51 are disposed along, and over the whole width of, the front and the rear ends of the exterior laminate 11 between the outer sheet 12 and the inner sheet 13 in their stretched state to form a waist portion 5 along the waist opening. The waist elastic members 51 are arranged such that those on the front section A and those on the rear section B overlap at their ends or continue to each other at the side seals S when the side edges A1 and A2 of the front section A and the side edges B1 and B2 of the rear section B meet and are sealed together. As a result, there is formed a substantially continuous loop of waist gather along the waist opening as shown in FIG. 1.

The exterior laminate 11 extends outward from both longitudinal ends of the absorbent body 10, and the extension is folded back to cover each of the longitudinal ends of the absorbent body 10 (specifically, the longitudinal ends of the topsheet 2 are covered with the extensions). Alternately, the outer sheet 12 is made longer than the inner sheet 13, extending outward from the longitudinal ends of the inner sheet 13, and the extensions are folded back to cover the longitudinal ends of the absorbent body 10.

Leg elastic members 61a and 61b are disposed along the inward curves on both sides of the exterior laminate 11 to form a pair of leg portions 6. The leg elastic members 61a and 61b are sandwiched between the outer sheet 12 and the inner sheet 13 and fixed in their stretched out state by prescribed fixing means. The leg elastic member 61a and the leg elastic member 61b overlap at one of their ends in the crotch section C. The other end of each of the leg elastic members 61a and 61b is located at the side edge A1 or A2 of the front section A and the side edge B1 or B2 of the rear section B, respectively. The leg elastic members 61a and 61b are arranged such that their ends located at the side edges A1 or A2 of the front section A and their ends located at the side edge B1 or B2 of the rear section B overlap with each other or continue to each other when the side edges A1 and A2 of the front section A and the side edges B1 and B2 of the rear section B are joined together. As a result, there is formed a substantially continuous loop of leg gather along each of the leg openings as shown in FIG. 1.

The diaper 1 has a number of elastic members extending in the diaper width direction between the waist portion 5 and the leg portions 6 in each of the front section A and the rear section B. First elastic members 71a are disposed between the waist portion 5 and leg portions 6 to form a first portion 71, and second elastic members 72a are arranged between the first portion 71 and the leg portions 6 to form a second portion 72. The first portion 71 and the second portion 72 extend in the diaper width direction. The first portion 71 is located between the waist portion 5 and the leg portions 6. The second portion 72 is located between the first portion 71 and the leg portions 6.

All the first elastic members 71a and the second elastic members 72a are fixed in their stretched out state between the outer sheet 12 and the inner sheet 13 of the exterior laminate 11. The first elastic members 71a are arranged such that their ends located at the side edges A1 or A2 of the front section A and their ends located at the side edge B1 or B2 of the rear section B overlap with each other or continue to each other when the side edges A1 and A2 of the front section A and the side edges B1 and B2 of the rear section B are joined together. The second elastic members 72a are arranged in the same way. As a result, there is formed a below-waist gather in the first portion 71 and the second portion 72 in the front section A as illustrated in FIG. 1 and also, while not shown, in the rear section B.

Each of the first elastic members 71a and the second elastic members 72a extends between the lateral sides of the diaper 1 (i.e., the lateral side edges of the exterior laminate 11) and the lateral, long side edges of the absorbent core 4. Substantially neither the first elastic members 71a nor the second elastic members 72a exists in the area where the absorbent core 4 exists. That is, the gathers formed in the first portion 71 and the second portion 72 are between the lateral sides of the diaper 1 and the lateral side edges of the absorbent core 4. There is no gathers in the area where the absorbent core 4 is disposed. Therefore, contraction of the exterior laminate 11 due to contraction of the first elastic members 71a and the second elastic members 72a does not occur in the area where the absorbent core 4 exists, so that the diaper 1 not only keeps its neat appearance but exhibits its full absorption capacity.

The elastic members used in the diaper 1 according to the present embodiment preferably include natural rubber, polyurethane resins, foamed urethane resins, extensible nonwoven fabrics, and hot-melt extensible materials molded into a string, a tape, a net or film.

Figure 4:
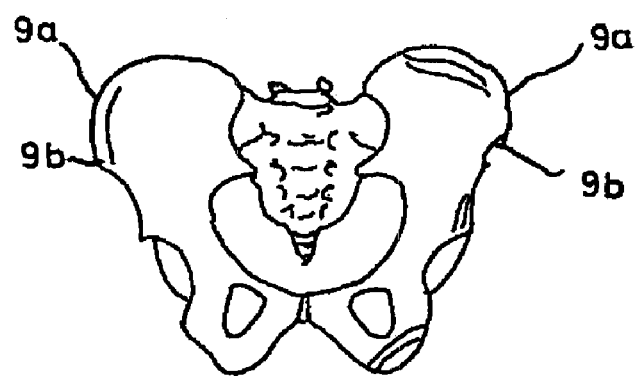
FIG. 4 is an illustration of the ilia.

According to the present embodiment, the first portion 71 of the diaper 1 while worn exerts a pressure of 1.1 to 2.5 kPa on a wearer's body. The first portion 71 is preferably formed in the region of the diaper 1 which, while worn by a wearer, is applied to the part of the wearer's body between the left and the right iliac crests and the left and the right anterior superior iliac spines. The part of a wearer's body will sometimes be referred to the upper iliac region. "Iliac crest" and "anterior superior iliac spine", which are anatomical terms, mean the sites indicated by the reference numerals 9a and 9b, respectively, in FIG. 4. In order to prevent a pull-on diaper from sliding down, particularly to prevent a pull-on diaper worn by a child from sliding down or drooping at the waist, it has been considered effective to increase the constrictive pressure of the elastic members disposed in the waist portion thus bringing the pull-on diaper into close contact with a wearer's body as exemplified by the design of JP-A-U-6-421 supra. On the contrary, as a result of investigation seeking for a solution of the problem that a pull-on diaper tends to slide down while worn, an increase in the constrictive pressure of the portion corresponding to the wearer's upper iliac region was found to be more effective than an increase in the constrictive pressure of the waist portion. The reason is as follows. Because a diaper wearer, especially a child from a baby to a toddler has a protruding abdomen as a physical characteristic, an increased constrictive pressure of the waist of a pull-on diaper applied around the periphery of the protruding belly gradually makes the waist of the diaper to constrict, thereby causing the diaper to droop until it fits the contour of the wearer.

Figure 5:
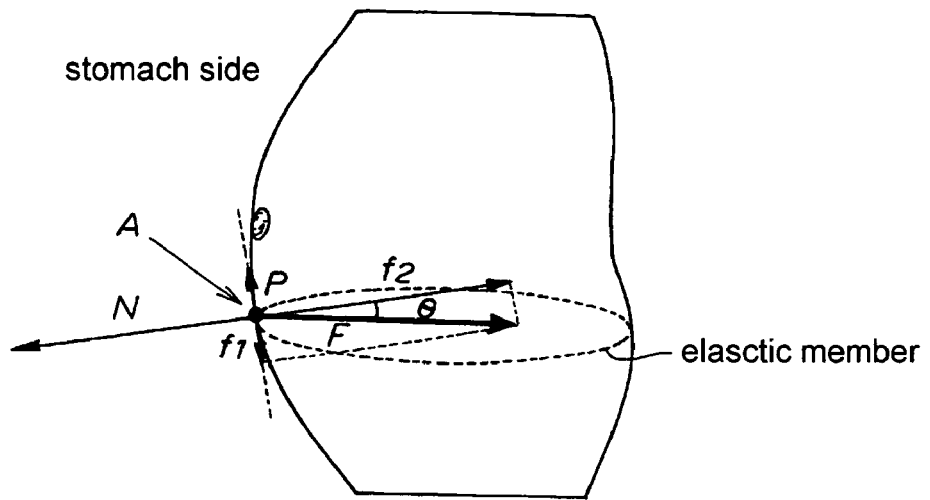
FIG. 5 illustrates how to calculate the sliding force around the waist of a wearer.

FIG. 5 is an illustration of a child's abdomen comparing a child's body in a standing posture to a circular cone. In FIG. 5, $\theta$ is an angle between a normal N to the tangent at a waist point (point A) and a horizon; F represents a constrictive force of an external elastic body; P represents a frictional force attributed to F; f1 represents a sliding force attributed to F; and f2 represents a normal force. $f1 = F \sin\theta$, and $P = \nu N = \nu f2 = \nu F \cos\theta$ (where $\nu$ represents a coefficient of friction). Accordingly, a downward sliding force Z at point A is represented by formula:

$$Z = f1 - P = F\sin\theta - \nu F\cos\theta = F(\sin\theta - \nu\cos\theta)$$

It is understood from the formula above that a larger constrictive force (F) creates a larger sliding force when the waist of a diaper is in a condition ready to slide down.

As stated previously, the pressure of the first portion 71 exerted while the diaper 1 is worn is from 1.1 to 2.5 kPa. If that pressure is less than 1.1 kPa, it is difficult to keep the first portion 71 on the upper iliac region of the wearer, and the diaper 1 easily moves down, resulting in a dull, droopy appearance. Drooping of the diaper 1 is conspicuous particularly around the crotch, thus causing urine and fecal leakage. If that pressure is more than 2.5 kPa, on the other hand, the diaper 1 will constrict the wearer's body too strong, not only giving discomfort to the wearer but making diapering difficult. To prevent the diaper 1 from sliding down more effectively and to improve the appearance of the diaper 1 while worn and the ease of changing diapers 1, it is preferred that the pressure of the first portion 71 while worn range from 1.1 to 2.0 kPa, more preferably from 1.2 to 1.8 kPa.

The pressure exerted by the first portion 71 of the diaper 1 while worn is adjustable by controlling the material, thickness, elongation, and the distance of spacing of the first elastic members 71a.

Measurement of the wearing pressure of the first portion 71 of the diaper 1 is carried out on the diaper 1 put on a cylinder having a circumference of 500 mm with a clothing pressure measuring device (air-pack type contact surface pressure measuring system AMI 3037-2, available from AMI Techno Co., Ltd.) as follows.

Measurement of Pressure by First Portion 71:

An air pack (pressure sensor) having a diameter of 15 mm is placed with its center even with the waist opening edge of the diaper, and the wearing pressure P1 is measured. The air pack setting position in the width direction of the diaper is nearly the middle between the lateral side edges of the diaper and the lateral side edges of the absorbent core 4 (see FIG. 3). Subsequently, the air pack is successively shifted down by 5 mm along the diaper length direction to measure the wearing pressure (P2, P3, P4, ..., Pn) for every shift until it reaches the same level as the lower end of the side seals S. The measurement is conducted at four points in total on the same vertical position (the same position in the diaper length direction) per each of the front section A and the rear section B, two in the left side and two in the right side of the absorbent core 4, to obtain an average wearing pressure at a specific vertical position of the front section A or the rear section B. The vertical distance between two out of the n sites of measurement between which all the measured pressures P are within a range of 1.1 kPa and 2.5 kPa is taken as the width of the first portion 71. When, for instance, P3 to P6 fall within the recited range, the width of the first portion 71 is (6−3)×5=15 mm. In that case, the mid point between the measuring site of P3 and that of P6 is the widthwise middle of the first portion 71.

The mean circumference of the waist of children at which the diaper 1 of the present embodiment is primarily targeted is about 500 mm, which is selected as the diameter of the cylinder. The term "circumference of the waist" as used herein is an average of the circumference measured of a child in a standing posture and that of a child in a sitting posture, taking into consideration a probable change in the circumference at the waist with the change in body posture.

There is a certain distance between the iliac crest and the anterior superior iliac spine of a wearer. That is, the upper iliac region has a certain width. The diaper 1 is effectively kept from moving down by applying the first portion 71 of the diaper 1 to the upper iliac region. From that viewpoint, the first portion 71 of the diaper 1 according to the present embodiment has a width W1, measured in the diaper length direction, of 15 to 35 mm. With the width W1 being 20 to 35 mm, particularly 25 to 30 mm, the diaper 1 will be kept in place more effectively, and the appearance of the diaper 1 while worn and the ease of diapering with the diaper 1 will be further improved.

Figure 6:
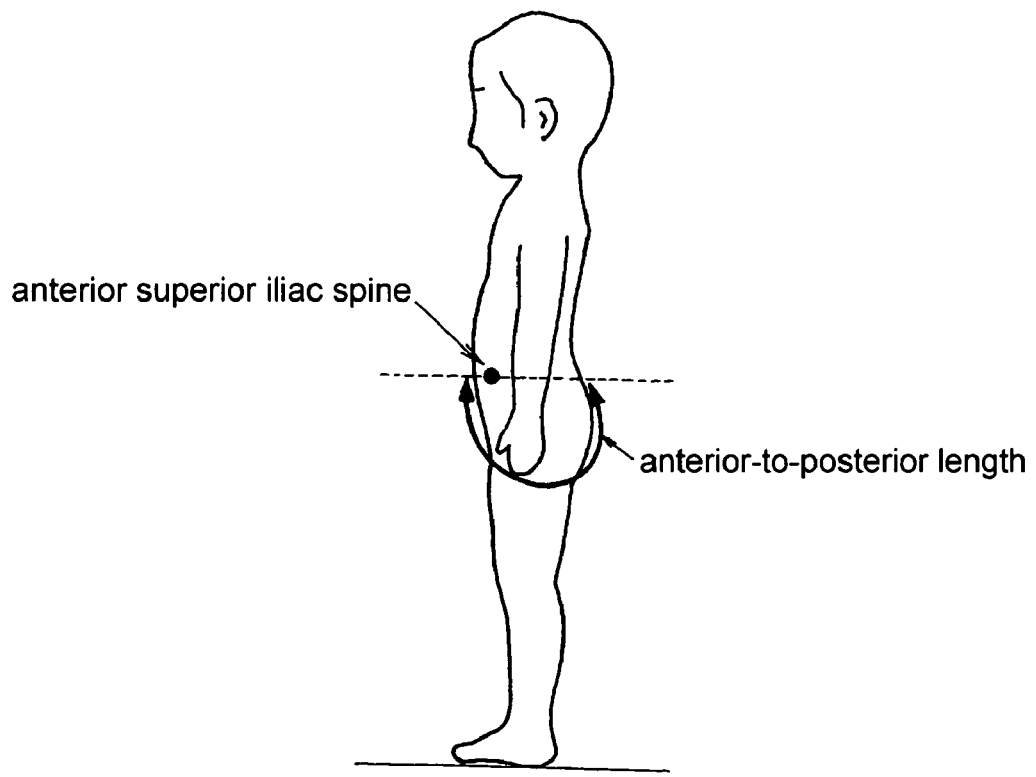
FIG. 6 illustrates how to measure the front-to-rear length at the height of the anterior superior iliac spine.

In order for the first portion 71 to be applied to the part between the iliac crest and the anterior superior iliac spine (i.e., the upper iliac region), the relation between the size of the diaper 1 and the physical size of a wearer is of importance. Considering children from older baby to toddlers, primarily targeted wearers, for instance, the first portion 71 can successfully be applied to the upper iliac region when the distance K1 from the widthwise middle of the first portion 71 (i.e., the middle of the first portion 71 along the diaper length direction) of the front section A to the longitudinal centerline CL of the diaper 1 is 180 to 220 mm as measured in the opened and stretched out state of the diaper 1, and when the distance K2 from the widthwise middle of the first portion 71 (i.e., the middle of the first portion 71 along the diaper length direction) of the rear section B to the longitudinal centerline CL of the diaper 1 is 180 to 220 mm as measured in the opened and stretched out state of the diaper 1. The K1 and K2 values had been decided as a result of physical measurement of about 350 children for whom pants type pull-on diapers are primarily designed. These values will be described more specifically by referring to FIG. 6 presenting a side view of a standing child. The mid point between, and at the height of, the left and right anterior superior iliac spines in the anterior view of the child is designated "anterior center". The mid point similarly defined but in the posterior view of the child is designated "posterior center". The length from the anterior center via the crotch to the posterior center is designated "anterior-to-posterior length". The sum of the anterior-to-posterior length and an allowance for a diaper thickness is divided by two to give the above-recited K1 and K2 values. The same applies to the second aspect of the invention. In order to apply the first portions 71 to the upper iliac region of a wearer more successfully, the distances K1 and K2 are preferably 185 to 215 mm, more preferably 190 to 215 mm.

Figure 7A:
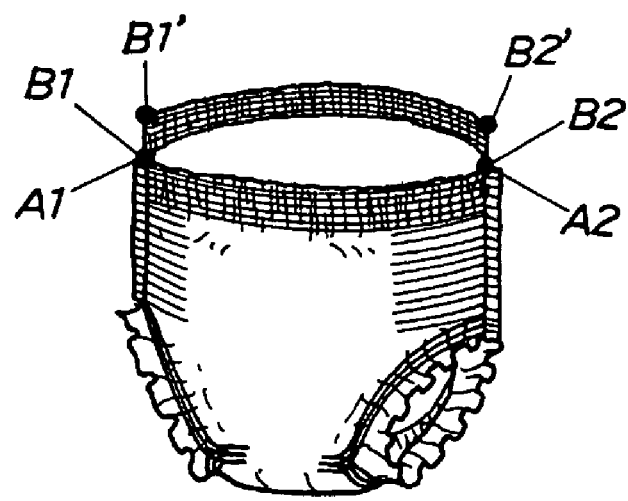
FIG. 7(a) is a perspective illustrating another embodiment of the diaper according to the present invention.
Figure 7B:
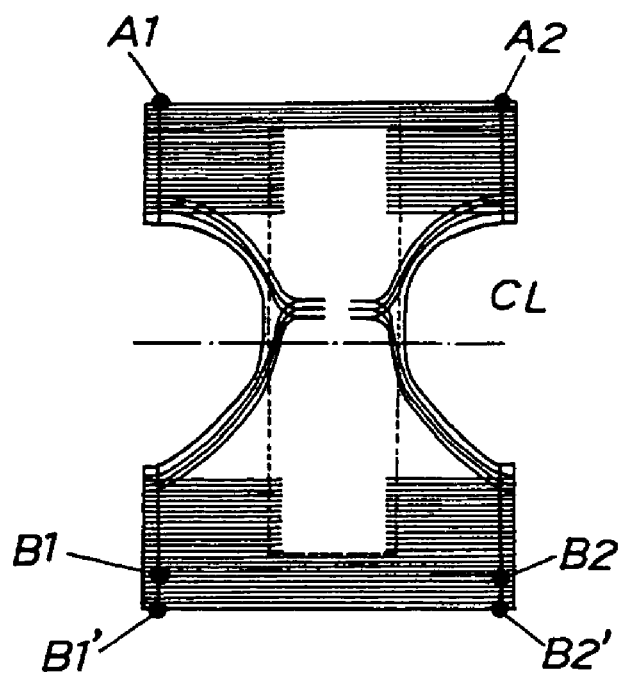
FIG. 7(b) is a plan of the diaper of FIG. 7(a) in its opened and stretched out state.

The first portion exists in each of the front section A and the rear section B. The wearing pressure of the first portion in the front section A and that of the rear section B do not need to be quite the same. As long as the wearing pressure of each of the first portions 71 in the front section A and the rear section B is in a range of from 1.1 to 2.5 kPa, the elastic members arranged on the front side and those on the rear side of the diaper may differ in material, thickness, elongation, and distance of spacing. Nevertheless, excessive configurational difference between the front section A and the rear section B can result in a dull appearance of the diaper because the side seals S of the exterior laminate 11 may come to the front or rear side of the diaper worn. Hence, it is desirable that the ratio of the difference between a higher wearing pressure of the first portion 71 of either one of the front section A and the rear section B and a lower wearing pressure of the first portion 71 of the other section to the higher wearing pressure be within 30%.

Where the diaper 1 of the present invention has its front section A and the rear section B sealed together with the upper and the lower ends of the side edges A1 and A2 of the front section A and B1 and B2 of the rear section B substantially coinciding with each other, the term "longitudinal centerline CL" as used in the present invention inclusive of the first and the second aspects means the straight line parallel to the diaper width direction (which is perpendicular to the diaper length direction (L in FIG. 3)) and passing the mid point between the upper end of A1 and the upper end of B1 of the diaper 1 in the opened and stretched out state (see FIG. 3). Unlike that, there is a case where, as shown in FIGS. 7(*a*) and 7(*b*), the side edges A1 and A2 of the front section A are not sealed with side edges B1' and B2' of the rear section B but with side edges B1 and B2 of which the upper ends (in the sealed state shown in FIG. 7(*a*)) are positioned lower than those of the side edges B1' and B2', respectively. In that case, the longitudinal centerline is drawn in the same manner as described above, except that the band defined by the upper ends (in the sealed state) of the side edges B1' and B2' and the upper ends (in the sealed state) of the side edges B1 and B2 is assumed not to exist.

The whole length L of the exterior laminate 11 in its opened and stretched out state is selected arbitrarily. Nevertheless, L is preferably 460 to 520 mm for giving a wearer comfort during and after use and for preventing sliding down during use. To give a user or a wearer a sense of security against leakage, it is desirable for the diaper to completely cover the navel. From that viewpoint, L is more preferably 490 to 580 mm.

As stated, the diaper 1 of the present embodiment is kept in position while worn mostly by the constrictive force exerted by the first elastic members 71*a* disposed in the first portions 71. In other words, the elastic members disposed in the waist portion 5 do not make a major contribution to keeping the diaper 1 in position on a wearer's body unlike the conventional pull-on diapers. On the contrary, an increased constrictive force of the waist portion 5 helps the diaper 1 move down. From this point of view, the pressure imposed to the wearer's body by the waist portion 5 is in the range of from 0.3 to 1.5 kPa, which range is lower than that of conventional pull-on diapers. It is preferred that the pressure of the waist portion 5 be lower than the average pressure of the first portions 71 by 0.5 to 1.0 kPa. The waist portion 5 having its constrictive pressure falling within the recited range offers another advantage that the waist portion 5 is easy to widen, which makes diapering easy. If the pressure of the waist portion 5 is less than 0.3 kPa, the natural length around the waist before being worn is so long that the diaper can have a poor appearance.

To ensure the diaper is kept in place, the wearing pressure of the waist portion 5 is preferably 0.4 to 1.2 kPa, more preferably 0.4 to 1.0 kPa. The pressure of the waist portion 5 is measured in the same manner as used to measure the pressure of the first portions 71. That is, a 500 mm circumference cylinder is put in the diaper through the waist opening. A 15 mm diameter air pack of a clothing pressure measuring device is placed with its center positioned 15 mm below the waist opening edge to measure the wearing pressure. The measurement is conducted at 10 points at a 50 mm interval along the circumference. The average of the ten measurements is taken as a wearing pressure of the waist portion. Where the waist opening edge of the front section and that of the rear section are not even as in the embodiment of FIGS. 7(a) and 7(b), the position nearest to the waist opening edge in the overlap of the front and the rear sections is taken as the waist opening edge. The pressure exerted by the waist portion 5 of the diaper 1 while worn is adjustable by controlling the material, thickness, elongation, and the distance of spacing of the waist elastic members 51. Where the pressure by the waist portion 5 is in the range of the pressure by the first portion 71, the position of the measurement is included under the first portion 71.

The diaper 1 preferably have leg elastic members 61a and 61b arranged in their stretched out state substantially along each of the leg openings. The pressure exerted by each leg portion 6 where the elastic members 61a and 61b are arranged while the diaper 1 is worn preferably ranges from 1.0 to 2.4 kPa, more preferably 1.2 to 2.2 kPa. With the pressure by the leg portions 6 falling within that range, the edge of the leg openings gives a snug fit to the groins to effectively prevent leakage around the wearer's leg. When the crotch portion of the diaper 1 gains weight due to discharge of urine or feces, the absorbent body in the crotch section is kept in contact with the wearer's crotch by that pressure, thereby keeping the appearance of the diaper 1 and preventing leakage of urine and feces. Thus, the pressure by the leg portions 6 is effective in maintaining the diaper 1 in good condition while worn.

The wearing pressure exerted by the leg portion 6 is measured as follows with the same air-pack type contact surface pressure measuring system as used in the measurement of the pressure by the waist portion 5. A 300 mm circumference cylinder is inserted through the leg opening. A 15 mm diameter air pack is placed beneath the leg portion 6 where the elastic member 61a or 61b is disposed. The measurement is conducted at 6 points at a 50 mm interval along the circumference per leg portion 6. Where there are two or more elastic members 61a or 61b, the point of measurement is the widthwise middle of the area where the elastic members are arranged. The average of the 12 measurements (6 in the left leg portion and 6 in the right leg portion) is taken as a wearing pressure of the leg portion 6. Where there is no, or only partial, elastic members around the leg openings, the wearing pressure of the area where the side cuff elastic member 81 is disposed measured in the part corresponding to each leg portion is taken as a pressure by the leg portion. The mean circumference of the thighs (at the largest point) of children at which the diaper 1 of the present embodiment is primarily targeted is about 300 mm, which is selected as the diameter of the cylinder.

The diaper 1 preferably has a wearing pressure of 0.2 to 0.8 kPa, more preferably 0.3 to 0.6 kPa in the area except the first portions 71, the waist portion 5, and the leg portions 6, for example, the second portions 72 between the first portions 71 and the leg portions 6. With that wearing pressure, the diaper 1 is kept in close and comfortable contact with the wearer's body thus effectively preventing leakage. The second portions 72 is applied to the body below the upper iliac region, namely the lower abdominal region. The second portion 72 preferably has a width W2 (measured in the diaper length direction) of 40 to 70 mm, more preferably 45 to 65 mm.

Comparing the wearing pressure between different portions of the diaper 1, it is preferred that the wearing pressure increase in the order of the second portion 72, the waist portion 5, and the first portion 71. The diaper with such an order of wearing pressure among the portions succeeds in keeping itself in place with a snug and comfortable fit to the wearer's body while worn thereby providing effective protection against leakage.

As is understood from the foregoing description, a pull-on diaper is effectively prevented from sliding down with the pressure applied to the upper iliac region of the wearer's body falling within a range of from 1.1 to 2.5 kPa while worn. The first elastic members disposed in the first portion are means for adjusting the pressure applied to the upper iliac region. Nevertheless, the means for the pressure adjustment is not limited to the elastic member. For example, the part of a diaper worn by a wearer that corresponds to the upper iliac region may be tightened with a belt or the like so that the wearing pressure on the upper iliac region of the wearer may fall in the recited range. In other words, the present invention includes in its scope a method of diapering in addition to the aforementioned pull-on disposable diaper design and configuration. More specifically, the present invention provides a method of diapering using a pull-on disposable diaper having a liquid permeable topsheet, a water repellant backsheet, a liquid retentive absorbent core interposed between the topsheet and the backsheet, and an exterior laminate disposed on the backsheet side, the lateral edges of the exterior laminate on both sides of one of the longitudinal ends and those of the other longitudinal end being joined together to form a waist opening and pair of leg openings. The method includes putting the pull-on diaper on a wearer and tightening the part of the diaper applied to the part of the wearer's body from the iliac crest to the anterior superior iliac spine with a prescribed means to apply a wearing pressure of 1.1 to 2.5 kPa to that part of the wearer's body.

Figure 8:
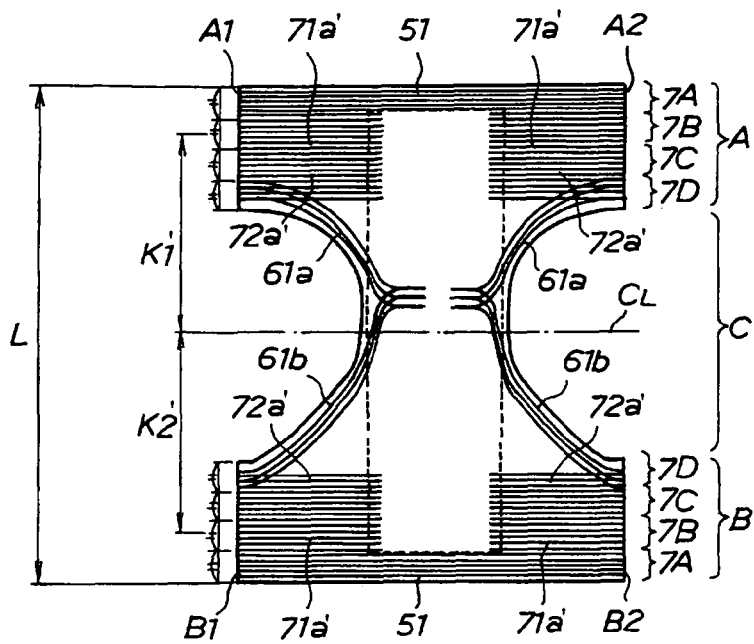
FIG. 8 is a plan illustrating an embodiment of the disposable diaper according to the second aspect of the invention in its opened and stretched out state.

An embodiment of the second aspect of the invention will then be described with reference to FIG. 8. The description of the first aspect applies appropriately to those particulars that are not referred to hereunder. Reference numerals common to FIGS. 1 to 7 and 8 represent the same elements.

As depicted in FIG. 8, the region between the waist opening and the pair of leg openings in each of the front section A and the rear section B of the diaper 1 in its sealed state (the term "sealed state" has been defined above) has hypothetically quartered first to fourth subsections having equal widths in the diaper length direction. The four subsections are designated the first subsection 7A, the second subsection 7B, the third subsection 7C, and the fourth subsection 7D from the waist opening to the leg openings. Each of the subsections 7A through 7D extends in the diaper width direction. The subsection 7A contains waist elastic members 51, and the subsection 7D contains leg elastic members 61a and 61b. The subsections 7B and 7C between the subsections 7A and 7D each contain a number of elastic members extending in the diaper width direction. Of these elastic members, those lying in the subsection 7B will be called "first elastic members 71a'", and those laying in the subsection 7C "second elastic members 72a'".

Each of the first elastic members 71a' and the second elastic members 72a' extends between the lateral side edge of the diaper 1 (i.e., the lateral side edge of the exterior laminate 11) and the lateral side edges of the absorbent core 4. Substantially neither the first elastic members 71a' nor the second elastic members 72a' exists in the area where the absorbent core 4 exists. That is, the gathers formed in the subsections 7B and 7C are between the lateral side edges of the diaper 1 and the lateral side edges of the absorbent core 4. There is no gathers in the area where the absorbent core 4 is disposed. Therefore, contraction of the exterior laminate 11 due to contraction of the first elastic members 71a' and the second elastic members 72a' does not occur in the area where the absorbent core 4 exists, so that the diaper 1 not only keeps its neat appearance but exhibits its full absorption capacity. The configuration of the diaper according to the present invention is not limited to the present embodiment nevertheless. For instance, the first elastic members 71a' and the second elastic members 72a' may be disposed over substantially the whole circumference of the diaper 1.

While the diaper 1 of the present embodiment is worn, the subsection 7B exerts an average wearing pressure of 0.9 to 1.8 kPa and a maximum wearing pressure of 2.5 kPa or lower. The subsection 7B is preferably formed in the region of the diaper 1 adapted to be applied to the part of the wearer's body between the iliac crest and the anterior superior iliac spine (i.e., the upper iliac region). In order to prevent a pull-on diaper from moving down during use, to an increase in the constrictive pressure of the region corresponding to the wearer's upper iliac region was found to be more effective than an increase in the constrictive pressure of the waist portion, i.e., the subsection 7A. The reason is that a child, a diaper wearer, has a protruding abdomen as a physical characteristic as mentioned previously.

As stated, the average and the maximum wearing pressures of the subsection 7B are 0.9 to 1.8 kPa and 2.5 kPa or lower, respectively. If the average wearing pressure of the subsection 7B is less than 0.9 kPa, it is difficult to keep the subsection 7B on the wearer's upper iliac region, and the diaper 1 easily slides down, resulting in a dull, droopy appearance. Drooping of the diaper 1 is conspicuous particularly around the crotch, thus causing urine and fecal leakage. If that pressure is more than 1.8 kPa, on the other hand, the subsection 7B will not only uncomfortably constrict the wearer's body but make diapering difficult. Additionally, local pressure application can leave a mark of the elastic member on the wearer's skin. To avoid such a disadvantage, it is meaningful that the maximum pressure exerted by the subsection 7B should be 2.5 kPa or lower. To keep the diaper 1 in place more effectively and to improve the appearance of the diaper 1 while worn and the ease of changing diapers 1, it is preferred that the wearing pressure of the subsection 7B range from 0.8 to 1.6 kPa, more preferably from 0.9 to 1.5 kPa. To ensure prevention of a pressure mark on the skin by the elastic member, the maximum wearing pressure of the diaper 1 is 2.0 kPa or lower, more preferably 1.8 kPa or lower.

The average pressure and the maximum pressure exerted by the subsection 7B of the diaper 1 while worn is adjustable by controlling the material, thickness, elongation, and the distance of spacing of the first elastic members 71a'.

Measurement of the average and the maximum pressures of the subsection 7B of the diaper 1 is carried out on the diaper 1 put on a cylinder having a circumference of 500 mm with a clothing pressure measuring device (air-pack type contact surface pressure measuring system AMI 3037-2, available from AMI Techno Co., Ltd.) as follows.

Measurement of Pressure by Subsection 7B:

A 500 mm circumference cylinder is put in the diaper 1 through the waist opening. A 15 mm diameter air pack is placed with its center positioned on the border between the subsections 7A and 7B to measure the wearing pressure P1. The air pack setting position in the width direction of the diaper is nearly the middle between the lateral side edges of the diaper and the lateral side edges of the absorbent core 4 (see FIG. 8). Subsequently, the air pack is successively shifted down by 5 mm in the diaper length direction within the second subsection 7B to measure the wearing pressure (P2, P3, P4, . . . , Pn) for every shift. The measurement is conducted at four points in total on the same vertical position (the same position in the diaper length direction) per front section or rear section, two in the left side and two in the right side of the absorbent core 4. An average wearing pressure and the maximum wearing pressure of the subsection 7B are obtained from the measurements.

There is a certain distance between the iliac crest and the anterior superior iliac spine of a wearer. That is, the upper iliac region of a wearer has a certain width. The diaper 1 is effectively kept from sliding down by applying the subsection 7B of the diaper 1 to the upper iliac region of a wearer. To achieve this, the side seals S of the diaper 1 according to the present embodiment have a length of 90 to 140 mm. The length of the side seals S is preferably 95 to 135 mm, more preferably 95 to 130 mm. With the length of the side seals S being in the preferred range, the diaper 1 will be kept in place more effectively, and the appearance of the diaper 1 while worn and the ease of diapering with the diaper 1 will be further improved.

In addition to the length of the side seals S, the total length L of the diaper 1 in its opened and stretched out state is limited to a range of 440 to 530 mm. As long as the subsection 7B is formed in the region which is adapted to be applied to the upper iliac region of a wearer, the portion above the subsection 7B, namely the subsection 7A, is not responsible for the diaper's sliding down. On the contrary, a strong constrictive pressure by the subsection 7A causes the subsection 7A to slide down near to the iliac crest. For the subsection 7A to be wider (in the diaper length direction) than necessary means that the portion which is liable to slide down has a large width. Accordingly, in order to keep the diaper in position and to secure a neat and natty appearance, the subsection 7A is desirably as narrow as possible. Nevertheless, regarding a diaper as a kind of clothing, a certain width would be required of the subsection 7A. When the total length L of the diaper 1 in its opened and stretched out state is 440 to 530 mm, the diaper 1 successfully has its subsection 7B applied to the upper iliac region of a wearer's body and is therefore prevented from sliding down while giving a user or a wearer a sense of security and assuring a neat appearance of the diaper as clothing. To ensure the sense of security, to improve the appearance, and to prevent the diaper sliding down more effectively, the total length L of the diaper 1 is preferably 450 to 520 mm, more preferably 460 to 515 mm.

In order for the subsection 7B to be applied to the upper iliac region of a wearer's body, the relation between the size of the diaper 1 and the physical size of the wearer is of importance. Considering a child, a primarily targeted wearer, for instance, the subsection 7B can successfully be applied to the upper iliac region when the distance K1' from the widthwise middle of the subsection 7B (i.e., the middle of the subsection 7B along the diaper length direction) of the front section A to the longitudinal centerline CL of the opened and stretched out diaper 1 is 180 to 220 mm, and when the distance K2' from the widthwise middle of the subsection 7B (i.e., the middle of the subsection 7B along the diaper length direction) of the rear section B to the longitudinal centerline CL of the opened and stretched out diaper 1 is 180 to 220 mm. In order to apply the subsection 7B to the upper iliac region of a wearer's body more accurately, the distances K1' and K2' are preferably 185 to 215 mm, more preferably 190 to 215 mm.

The subsection 7B exists in each of the front section A and the rear section B. The wearing pressure of the subsection 7B in the front section A and that of the rear section B do not need to be quite the same. As long as the wearing pressure of each of the subsections 7B in the front section A and the rear section B is in a range of from 0.9 to 1.8 kPa, and the maximum of these wearing pressures is 2.5 kPa or lower, the elastic members arranged on the front side and those on the rear side of the diaper may differ in material, thickness, elongation, and distance of spacing. Nevertheless, excessive configurational difference between the front section A and the rear section B can result in a dull appearance of the diaper because the side seals S of the exterior laminate 11 may come to the front or rear side of the diaper worn. Hence, it is desirable that the ratio of the difference between a higher wearing pressure of the first portion 71 of either one of the front section A and the rear section B and a lower wearing pressure of the first portion 71 of the other section to the higher wearing pressure be within 30%.

The diaper 1 of the present embodiment is kept in position while worn mostly by the constrictive force exerted by the first elastic members 71a' disposed in the subsections 7B. In other words, the waist elastic members 51 mostly disposed in the subsection 7A do not make a major contribution to keeping the diaper 1 in position on a wearer's body. The average pressure imposed to the wearer's body by the subsection 7A is preferably in the range of from 0.3 to 1.2 kPa, which range is lower than that of conventional pull-on diapers. It is essential that the average pressure of the subsection 7A be lower than the average pressure of the subsection 7B. The subsection 7A having their constrictive pressure falling within the recited range offers another advantage that the waist opening is easy to widen, which makes diapering easy. If the pressure of the subsection 7A is less than 0.3 kPa, the natural length around the waist before being worn is so long that the diaper can have a poor appearance as clothing.

The diaper 1 is prevented from sliding down more effectively where the subsection 7A exert an average wearing pressure of 0.4 to 1.2 kPa, more preferably 0.5 to 1.1 kPa. The average wearing pressure of the subsection 7A can be measured in the same manner as for the measurement of the average wearing pressure of the subsection 7B. In some detail, a 500 mm circumference cylinder is put in the diaper 1 through the waist opening. A 15 mm diameter air pack is placed with its center positioned in the subsection 7A to measure the wearing pressure P1. The air pack setting position in the width direction of the diaper is nearly the middle between the lateral side edges of the diaper and the lateral side edges of the absorbent core 4. Subsequently, the air pack is successively shifted down by 5 mm in the diaper length direction within the first subsection 7 to measure the wearing pressure (P2, P3, P4, . . . , Pn) for every shift. The measurement is conducted at four points in total on the same vertical position (the same position in the diaper length direction) per front section or rear section, two in the left side and two in the right side of the absorbent core 4. An average wearing pressure of the subsection 7A is obtained from the resulting measurements. The average pressure of the subsection 7A is adjustable by controlling the material, thickness, elongation, and the distance of spacing of the waist elastic member 51.

It is preferred for the subsection 7C to exert a wearing pressure of 0.2 to 1.0 kPa, more preferably 0.3 to 0.8 kPa, in average, whereby the diaper 1 maintains a snug fit to the wearer's body with a moderate wearing pressure thus preventing leakage effectively. It is necessary that the pressure by the subsection 7C be lower than that by the subsection 7B. The subsection 7C is adapted to be applied to the wearer's body below the upper iliac region, namely the lower abdominal region. The pressure by the subsection 7C is determined in the same manner as for the measurement of the average wearing pressures by the subsections 7A and 7B. In some detail, a 500 mm circumference cylinder is put in the diaper 1 through the waist opening. A 15 mm diameter air pack is placed with its center positioned on the border between the subsections 7B and 7C to measure the wearing pressure P1. The air pack setting position in the width direction of the diaper is nearly the middle between the lateral side edges of the diaper and the lateral side edges of the absorbent core 4. Subsequently, the air pack is successively shifted down by 5 mm in the diaper length direction within the third subsection 7C to measure the wearing pressure (P2, P3, P4, . . . , Pn) for every shift. The measurement is conducted at four points in total on the same vertical position (the same position in the diaper length direction) per front section or rear section, two in the left side and two in the right side of the absorbent core 4. An average wearing pressure of the subsections 7C is obtained from the resulting measurements.

As mentioned above, the pressures of the subsections 7A and 7C are lower than the pressure of the subsection 7B. Comparing the wearing pressures of these three subsections, it is preferred that the wearing pressure increases in the order of the subsections 7C, 7A, and 7B. The diaper with such an order of wearing pressure among the subsections succeeds in keeping itself in place with a snug and comfortable fit to the wearer's body while worn thereby providing effective protection against leakage.

The diaper 1 of the present embodiment may have the same wearing pressure by the leg portions 6 as in the embodiment of the first aspect of the invention for the same reason as explained with respect to the first aspect.

While the present invention, inclusive of the first and the second aspects, has been described with particular reference to its preferred embodiments, it should be understood that the invention is not construed as being limited to these embodiments. For example, while in the foregoing embodiments the first elastic members 71a or 71a' or the second elastic members 72a or 72a' are disposed only in the areas between the lateral side edges of the diaper 1 and the lateral side edges of the absorbent core 4, they may overlap the absorbent core 4, or they may run over the whole circumference of the diaper 1. In these alternative configurations, the contractive force of the first and the second elastic members is also exercised in the area of the exterior laminate 11 on which the absorbent core 4 is placed. Even so, wrinkling of the exterior laminate 11 in that area can be averted by bonding that part of the exterior laminate 11 to the absorbent core 4 via a pressure-sensitive adhesive whereby the contraction of the elastic members can be suppressed by the stiffness of the core 4. Wrinkling of the exterior laminate 11 in the area where the core 4 is disposed may also be prevented by leaving these elastic members sandwiched in between the inner sheet 13 and the outer sheet 12 little fixed in the area where the core 4 is disposed.

Figure 9:
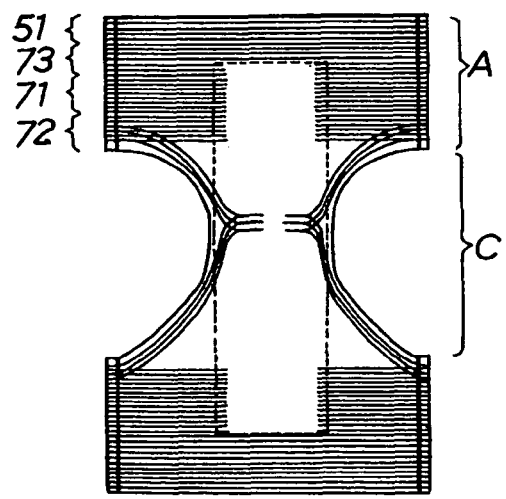
FIG. 9 is a plan of another embodiment of the diaper according to the invention in its opened and stretched out state.

The pull-on diaper of the first aspect of the invention includes any embodiment other than the one illustrated above, provided that (1) there is a below-waist portion between the waist portion and the leg portions, which, while worn by a wearer, applies a pressure of 1.1 to 2.5 kPa to the wearer's body, (2) the portion has a width of 15 to 35 mm, (3) the distance from the longitudinal centerline of the diaper in its opened and stretched out state to the widthwise middle of the portion in the front section is 180 to 220 mm, (4) the distance from the longitudinal centerline of the diaper in its opened and stretched out state to the widthwise middle of the portion in the rear section is 180 to 220 mm, and (5) the waist portion, while worn by a wearer, exerts a pressure of 0.3 to 1.5 kPa. In a conceivable embodiment, for example, the diaper may have a third portion 73 between the waist portion 5 and the first portion 71 as illustrated in FIG. 9.

Figure 10A:
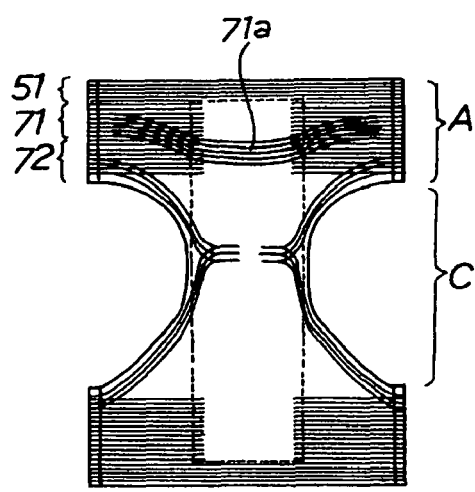
FIG. 10(a) and FIG. 10(b) each represent still another embodiment of the diaper according to the present invention in its opened and stretched out state.
Figure 10B:
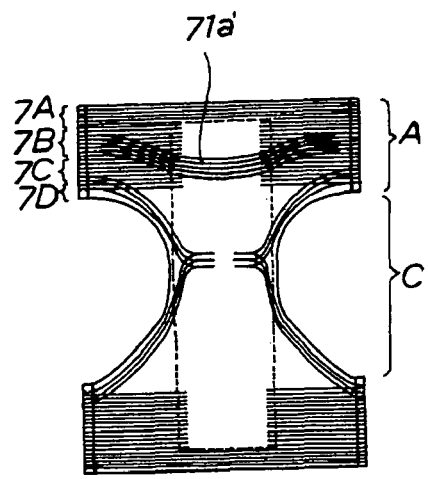

In the present invention, the pattern of arrangement of the first elastic members 71a or 71a' is not limited to the one adopted in the foregoing embodiments. For example, as shown in FIGS. 10(a) and 10(b), a plurality of the first elastic members 71a (or 71a') may be disposed over the whole width of the diaper in the front section A with their middle portion curving toward the crotch section C. Such a curved arrangement of the first elastic members 71a (or 71a') allows for the first elastic members stably exerting their constrictive force to the below-waist part of the wearer. In particular, such a curved arrangement helps provide a snug fit to the characteristic protruding abdomen of an older baby or a toddler. As a result, the diaper is effectively prevented from getting out of place in the vertical direction.

Figure 11A:
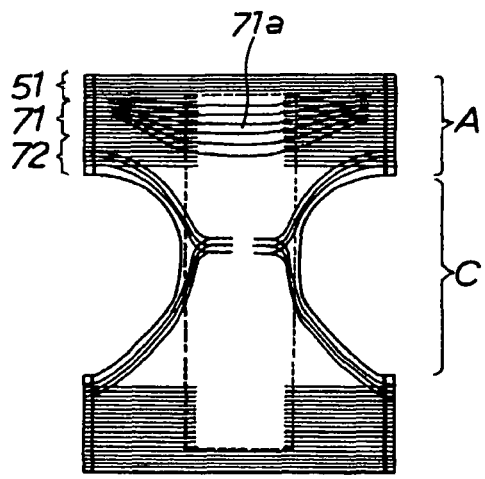
FIG. 11(a) and FIG. 11(b) each represent yet another embodiment of the diaper according to the present invention in its opened and stretched out state.
Figure 11B:
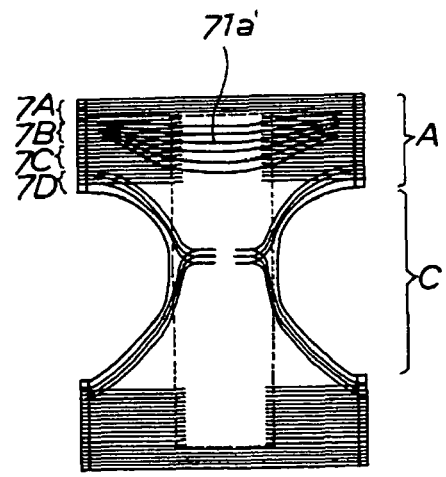

Still alternatively, as shown in FIGS. 11(a) and 11(b), a plurality of the first elastic members 71a (or 71a') may be disposed over the whole width of the diaper in the front section A with some of them curving to the crotch section C. It is preferable that the curvature radius of the curving elastic members decreases toward the crotch section C. Such a curved arrangement of the first elastic members allows for covering a wider area of the wearer's abdomen with the first elastic members to create constriction in not only the diaper width direction but the diaper length direction. As a result, the diaper is prevented from getting out of place in the vertical direction and, at the same time, there is created a force to pull up the widthwise middle portion of the front section of the diaper.

In the foregoing embodiments, the lateral side edges A1 and A2 of the front section A and the lateral side edges B1 and B2 of the rear section B are connected by sealing to form a pair of side seals S. Alternatively, they may be connected by means of various fasteners, such as snap fasteners, buttons, and hook and loop fasteners. The positions of the side seals or the positions of connecting the sides edges do not need to be right on the sides of a wearer's body and may be slightly off the sides to either the front or the back.

While the exterior laminate 11 used in the foregoing embodiments is composed of two sheets of nonwoven fabric as the outer and the inner sheets, the exterior laminate may be a combination of a nonwoven fabric sheet and a water repellent sheet.

While the diaper 1 according to the foregoing embodiments is composed of the exterior laminate 11 defining the diaper outline and the absorbent body 10 on the exterior laminate 11. Alternatively, the diaper of the present invention may be composed of the topsheet, the backsheet, and the absorbent core between the topsheet and the backsheet, wherein the topsheet and the backsheet define the outline of the diaper. The part of the diaper extending outward from each long side of the absorbent core in each of the front section and the rear section may be formed of an elastic panel.

While the nonwoven fabric forming the inner sheet 13 and the outer sheet 12 of the exterior laminate 11 is preferably water repellent, an embodiment in which only one of them is formed of water repellent nonwoven fabric is possible. Where the side cuffs 8 provide sufficient protection against leakage, both the inner and the outer sheets of the exterior laminate 11 may be formed of water permeable nonwoven fabric.

As described, the pull-on disposable diaper of the present invention hardly slides down while worn due to the wearer's movement. In particular, it hardly droops about the crotch. Therefore, the diaper keeps a neat appearance while worn, and the wearer is not hindered from moving smoothly by a droopy diaper. The elastic members disposed in the diaper are prevented from excessively constricting a wearer's body thus giving a comfort to a wearer. Since the diaper is prevented from sliding down, leakage of urine and feces is prevented.

The present invention will now be illustrated in greater detail with reference to Examples, but it should be understood that the invention is not deemed to be limited thereto.

Examples 1 and 2 (First Aspect) and Comparative Examples 1 to 4

Pull-on diapers shown in FIGS. 1 to 3 were made. The absorbent body 10 was fabricated using hydrophilic air-through nonwoven fabric having a weight of 25 g/m$^2$ as a topsheet 2 and a polyethylene sheet having a weight of 20 g/m$^2$ as a backsheet 3. The exterior laminate 11 was fabricated using water repellent air-through nonwoven fabric having a weight of 25 g/m$^2$ as an outer sheet 12 and water repellent spun-bonded nonwoven fabric having a weight of 18 g/m$^2$ as an inner sheet 13. The wearing pressures exerted by different portions were adjusted by changing the kind and the elongation of the elastic members used. The pressure by the first portion 71 in the front section A, the first portion 71 in the rear section B, and the waist portion 5 are shown in Table 1 below. The width W1 of the first portion 71, the distance K1 from the longitudinal centerline CL to the widthwise middle of the first portion 71, and the distance K2 from the longitudinal centerline CL to the widthwise middle of the first portion 71 are also shown in Table 1.

The resulting diapers were worn by 3 toddlers of one to two years of age and evaluated on the following items according to the following rating system. The results obtained are in Table 1.

(1) Ease of Diapering
  A: Easy
  B: Slightly easy
  C: Not easy (2) Position of the First Portion after 60 Minute Wearing
  A: Unchanged
  B: Slightly changed
  C: Changed (3) Position of the Waist Portion after 60 Minutes Wearing
  A: Unchanged
  B: Slightly changed
  C: Changed (4) Mark of Elastic Member of the First Portion on the Skin after 60 Minute Wearing
  A: No mark
  B: Slightly visible mark
  C: Visible mark (5) Position of Side Seals when the Diaper is Put on a Wearer
  A: In correct position (right on the sides of a wearer)
  B: Slightly off the sides
  C: Off the sides The diapers of Example 1 and Comparative Example 1 were further evaluated for the principal effects of the present invention, i.e., in terms of whether the first portion leaves a mark of elastic members on the skin in 60 minute wearing and whether the waist portion gets out of position in 60 minute wearing as follows. Mothers were asked to use 25 diapers each of Example 1 and Comparative Example 1 on their older babies or toddlers of from 11 to 37 months and to make a judgement on the diapers. The percentages of those who answered yes to question 1 "Does the diaper hardly leave a mark of elastic members on the skin?" and question 2 "Does the diaper hardly slip out of place while worn?" are shown in Table 2 below.

TABLE 1

|  | Pressure of 1st Portion (kPa) | | W1[1] (mm) | | K2[2] (mm) | K1[3] (mm) | Pressure of Waist Portion (kPa) | Ease of Diapering | After 60 Minute Wearing | | | |
|---|---|---|---|---|---|---|---|---|---|---|---|---|
|  | Front Section (A) | Rear Section (B) | Front Section (A) | Rear Section (B) | | | | | Position of 1st Portion | Position of Waist Portion | Mark of Elastic Member | Position of Side Seals |
| Example 1 | 1.5 | 1.4 | 25 | 27 | 202 | 199 | 0.8 | A | A | A | A | A |
| Example 2 | 1.9 | 1.5 | 32 | 18 | 185 | 205 | 1.0 | A | A | A | A | AB |
| Comparative Example 1 | 1.5 | 1.4 | 25 | 26 | 240 | 235 | 1.5 | B | C | C | B | A |
| Comparative Example 2 | 1.5 | 1.7 | 10 | 28 | 202 | 197 | 0.7 | A | C | C | C | AB |
| Comparative Example 3 | 3.2 | 3.3 | — | — | — | — | 0.8 | C | A | A | C | A |
| Comparative Example 4 | 1.5 | 1.4 | 42 | 39 | 199 | 201 | 0.8 | C | A | A | A | A |

[1] Width of the first portion.
[2] The distance from the longitudinal centerline to the widthwise middle of the 1st portion.
[3] The distance from the longitudinal centerline to the widthwise middle of the 1st portion.

As is apparent from the results in Table 1, all the diapers of Examples were easy to put on a wearer and kept in place during use. When put on a wearer, the diaper of Example 2 had its side seals positioned slightly off the sides to the front due to the configurational difference between the front and the rear sections, which was no problem for practical use.

In contrast, the diaper of Comparative Example 1, which corresponds to a conventional pull-on disposable diaper, moved down easily. The diaper of Comparative Example 2 also moved out of place because of insufficient width of the first portion. The diaper of Comparative Example 3, which had no portion corresponding to the first portion, was difficult to put on a wearer and easily left a mark of the elastic members on the wearer's skin. The diaper of Comparative Example 4 was difficult to put on a wearer on account of the too wide first portion.

TABLE 2

|  | Those Who Answered Yes to Question 1 | Those Who Answered Yes to Question 2 |
|---|---|---|
| Example 1 | 70% | 84% |
| Comparative Example 1 | 55% | 45% |

As can be seen from the survey results shown in Table 2, the diaper of Example 1 was highly supported by mothers with respect to freedom from pressure marks by the elastic members and freedom from slippage. In contrast, the diaper of Comparative Example 1 was supported by only about half of the mothers.

Example 3 (Second Aspect) and Comparative Examples 5 to 9

Pull-on diapers shown in FIGS. 1, 2, and 8 were made. The absorbent body 10 was fabricated using hydrophilic air-through nonwoven fabric having a weight of 25 g/m² as a topsheet 2 and a polyethylene sheet having a weight of 20 g/m² as a backsheet 3. The exterior laminate 1 was fabricated using water repellent air-through nonwoven fabric having a weight of 25 g/m² as an outer sheet 12 and water repellent spun-bonded nonwoven fabric having a weight of 18 g/m² as an inner sheet 13. The average wearing pressures exerted by the first subsection 7A, the second subsection 7B, and the third subsection 7C and the maximum wearing pressure by the first subsection 7A are shown in Table 3 below. The wearing pressures of these subsections were adjusted by changing the kind and the elongation of the elastic materials used. The total length and the side seal length of the diaper are also shown in Table 3.

The resulting diapers were worn by 3 toddlers of one to three years of age and evaluated on the following items in accordance with the following rating system. The results obtained are shown in Table 3.

(1) Ease of Diapering
   A: Easy
   B: Slightly easy
   C: Not easy (2) Position of the Second Subsection after 60 Minute Wearing
   A: Unchanged
   B: Slightly changed
   C: Changed (3) Position of the Waist Portion after 60 Minutes Wearing
   A: Unchanged
   B: Slightly changed
   C: Changed (4) Mark of Elastic Members of the Second Subsection on the Skin after 60 Minute Wearing
   A: No mark
   B: Slightly visible mark
   C: Visible mark (5) Appearance of Diaper Immediately after being Put on
   A: Neat
   B: Slightly neat
   C: Not neat (6) Appearance of Diaper after 60 Minute Wearing
   A: Neat
   B: Slightly neat
   C: Not neat The diapers of Example 3 and Comparative Example 9 were further evaluated for the principal effects of the present invention, i.e., in terms of whether the second subsection leaves a mark of elastic members on the skin in 60 minutes wearing and whether the waist portion gets out of position in 60 minutes wearing in the same manner as in Example 1. The results are shown in Table 4 below.

TABLE 3

| | Total Length (mm) | Side Seal Length (mm) | Pressure of 2$^{nd}$ Subsection (kPa) | | Average Pressure (kPa) | | Ease of Diapering | Position | | Mark of Elastic Member | Appearance of Diaper | |
| --- | --- | --- | --- | --- | --- | --- | --- | --- | --- | --- | --- | --- |
| | | | Average | Maximum | First Sub-section | Third Sub-section | | Second Subsection | Waist Portion | | Immediately after being Put on | After 60-minute Wearing |
| Example 3 | 490 | 120 | 1.2 | 1.6 | 0.9 | 0.5 | A | A | A | A | A | A |
| Comparative Example 5 | 540 | 170 | 1.3 | 1.7 | 0.8 | 0.4 | A | A | BC | A | C | C |
| Comparative Example 6 | 490 | 120 | 2.5 | 2 | 0.9 | 0.5 | C | A | A | C | A | A |
| Comparative Example 7 | 495 | 120 | 1.2 | 3 | 0.9 | 0.5 | BC | A | A | C | A | A |
| Comparative Example 8 | 490 | 120 | 1.4 | 1.5 | 2.1 | 0.4 | BC | A | C | A | A | A |
| Comparative Example 9 | 510 | 115 | 0.5 | 0.8 | 1.4 | 0.5 | AB | C | C | AB | A | BC |

As is apparent from the results in Table 3, the diaper of Example 3 is easy to put on a wearer, hardly slips out of place, and shows a good appearance after an elapse of some time as well as immediately after being put on. To the contrary, the diaper of Comparative Example 5 not only has a poor appearance due to its long total length and side seal length but easily droops at the waist; for the portion above the iliac crest is too long. Having a high average wearing pressure by the second subsection, the diaper of Comparative Example 6 is inconvenient to put on a wearer and easily leaves a mark of the elastic members on the wearer's skin. Similarly, the diaper of Comparative Example 7 is, having a high maximum wearing pressure by the second subsection, inconvenient to put on a wearer and liable to leave a mark of the elastic members. The diaper of Comparative Example 8 has a high average wearing pressure by the first subsection and is therefore apt to droop at the waist and difficult to put on a wearer.

TABLE 4

| | Those Who Answered Yes to Question 1 | Those Who Answered Yes to Question 2 |
| --- | --- | --- |
| Example 3 | 70% | 84% |
| Comparative Example 9 | 55% | 45% |

As can be seen from the survey results shown in Table 4, the diaper of Example 3 was highly supported by mothers with respect to freedom from pressure marks by the elastic members and freedom from slippage. In contrast, the diaper of Comparative Example 9 was supported by only about half of the mothers.

What is claimed is:

1. A pull-on disposable diaper having a waist opening and a pair of leg openings,
the diaper comprising a front section and a rear section, and having a first region and a second region at each of said front section and said rear section, said first and second regions being located between the waist opening and the leg openings, wherein said first regions are closer to said waist opening and said second regions are closer to said leg openings, and which, while worn by a wearer, apply a pressure to the wearer's body, and
a waist portion around said waist opening, while worn by a wearer, applies a pressure to the wearer's body that is less than the pressure to the wearer's body applied by said first region but more than the pressure to the wearer's body applied by said second region;
wherein upon wearing the diaper, said first regions are located in a region adapted to be applied to the part of a wearer from the iliac crest to the anterior superior iliac spine and said second regions are located in a region adapted to be applied to the part of a wearer below an upper iliac region of the wearer;
wherein said first regions apply a pressure of 1.1 to 2.5 kPa to the wearer's body and said waist portion applies a pressure of 0.3 to 1.5 kPa to the wearer's body.

2. The pull-on disposable diaper according to claim 1, wherein said first regions apply a pressure of 1.2 to 1.8 kPa to the wearer's body.

3. The pull-on disposable diaper according to claim 1, wherein said first regions have a width of 15 to 35 mm.

4. The pull-on disposable diaper according to claim 1, wherein the distance from a longitudinal centerline of the diaper in the opened and stretched out state to a widthwise middle of the first region in the front section is 180 to 220 mm.

5. The pull-on disposable diaper according to claim 1, wherein the distance from a longitudinal centerline of the diaper in the opened and stretched out state to a widthwise middle of the first region in the rear section is 180 to 220 mm.

6. The pull-on disposable diaper according to claim 1, wherein said waist portion applies a pressure of 0.4 to 1.0 kPa to the wearer's body.

7. The pull-on disposable diaper according to claim 1, wherein said second regions apply a pressure of 0.2 to 0.8 kPa to the wearer's body.

8. The pull-on disposable diaper according to claim 1, wherein said second regions have a width of 40 to 70 mm.

9. The pull-on disposable diaper according to claim 1, further comprising a crotch section and a first set of leg elastic members from said front section that overlaps a second set of leg elastic members from said rear section in the crotch section.

10. A pull-on disposable diaper having a waist opening and a pair of leg openings,
the diaper comprising a front section and a rear section, and having a first region and a second region at each of said front section and said rear section, said first and second regions being located between the waist opening and the leg openings, wherein said first regions are closer to said waist opening and said second regions are closer to said leg openings, and which, while worn by a wearer, apply a pressure to the wearer's body, a waist portion around said waist opening, and wherein a pressure applied by said first region is higher than a pressure applied by said waist portion, and a pressure applied by said first region is higher than a pressure applied by said second region; and wherein upon wearing the diaper, said first regions are located in a region adapted to be applied to the part of a wearer from the iliac crest to the anterior superior iliac spine and said second regions are located in a region adapted to be applied to the part of a wearer below an upper iliac region of the wearer;

wherein said first regions apply a pressure of 1.1 to 2.5 kPa to the wearer's body and said waist portion applies a pressure of 0.3 to 1.5 kPa to the wearer's body.

* * * * *